(12) United States Patent
Turovskiy et al.

(10) Patent No.: US 6,752,767 B2
(45) Date of Patent: Jun. 22, 2004

(54) LOCALIZATION ELEMENT WITH ENERGIZED TIP

(75) Inventors: Roman Turovskiy, San Francisco, CA (US); Ted Su, Mountain View, CA (US); Steven Kim, Los Altos, CA (US); Mani Prakash, Campbell, CA (US)

(73) Assignee: Vivant Medical, Inc., Mountain View, CA (US)

( * ) Notice: Subject to any disclaimer, the term of this patent is extended or adjusted under 35 U.S.C. 154(b) by 0 days.

(21) Appl. No.: 10/271,850

(22) Filed: Oct. 15, 2002

(65) Prior Publication Data

US 2003/0195433 A1 Oct. 16, 2003

Related U.S. Application Data

(60) Provisional application No. 60/373,190, filed on Apr. 16, 2002.

(51) Int. Cl.[7] .............................................. A61B 10/50
(52) U.S. Cl. ..................................................... 600/564
(58) Field of Search .......................... 604/22, 164, 264, 604/117; 600/434, 564, 431, 435; 128/899; 606/185, 116, 139, 159

(56) References Cited

U.S. PATENT DOCUMENTS

| 2,022,065 A | 11/1935 | Wappler |
| 2,047,535 A | 7/1936 | Wappler |

(List continued on next page.)

FOREIGN PATENT DOCUMENTS

| EP | 0 385 604 | 9/1990 |
| EP | 0 395 997 | 11/1990 |
| EP | 0 667 126 | 8/1995 |
| EP | 0 829 232 | 3/1998 |
| WO | WO 88/06864 | 9/1988 |
| WO | WO 92/12678 | 8/1992 |
| WO | WO 93/20767 | 10/1993 |
| WO | WO 93/20768 | 10/1993 |
| WO | WO 96/27328 | 9/1996 |
| WO | WO 99/04704 | 2/1999 |
| WO | WO 99/25248 | 5/1999 |
| WO | WO 99/43268 | 9/1999 |
| WO | WO 99/44506 | 9/1999 |
| WO | WO 99/58065 | 11/1999 |
| WO | WO 99/66834 | 12/1999 |
| WO | WO 00/10471 | 3/2000 |

(List continued on next page.)

OTHER PUBLICATIONS

Anonymous. (1987). *Homer Mammalok ® Breast Lesion Needle/Wire Localizer, Namic ® Angiographic Systems Division*, Glens Falls, New York, (Hospital products price list), 4 pages.

(List continued on next page.)

*Primary Examiner*—Max F. Hindenburg
*Assistant Examiner*—Brian Scott Szmal
(74) *Attorney, Agent, or Firm*—Morrison & Foerster LLP

(57) ABSTRACT

This invention is an improved tissue-localizing device with an electrically energized locator element for fixedly yet removably marking a volume of tissue containing a suspect region for excision. The electrical energizing of the locator element facilitates the penetration of the locator element in to subject's tissue and minimizes resistance due to dense or calcified tissues. At least one locator element is deployed into tissue and assumes a predetermined curvilinear shape to define a tissue border containing a suspect tissue region along a path. Multiple locator elements may be deployed to further define the tissue volume along additional paths defining the tissue volume border that do not penetrate the volume. Delivery of electric current may be achieved through monopolar or bipolar electronic configuration depending on design needs. Various energy sources, e.g. radio frequency, microwave or ultrasound, may be implemented in this energized tissue-localizing device.

2 Claims, 11 Drawing Sheets

U.S. PATENT DOCUMENTS

| | | |
|---|---|---|
| 3,330,278 A | 7/1967 | Santomieri |
| 3,351,463 A | 11/1967 | Rozner et al. |
| 3,516,412 A | 6/1970 | Ackerman |
| 3,714,851 A | 2/1973 | Orser |
| 3,753,700 A | 8/1973 | Harrison et al. |
| 3,890,977 A | 6/1975 | Wilson |
| 4,010,756 A | 3/1977 | DuMont et al. |
| 4,103,690 A | 8/1978 | Harris |
| 4,274,408 A | 6/1981 | Nimrod |
| 4,311,154 A | 1/1982 | Sterzer et al. |
| 4,341,226 A | 7/1982 | Peters |
| 4,402,328 A | 9/1983 | Doring |
| 4,592,356 A | 6/1986 | Gutierrez |
| 4,595,007 A | 6/1986 | Mericle |
| 4,612,940 A | 9/1986 | Kasevich et al. |
| 4,616,656 A | 10/1986 | Nicholson et al. |
| 4,633,880 A | 1/1987 | Osypka et al. |
| 4,658,836 A | 4/1987 | Turner |
| 4,665,906 A | 5/1987 | Jervis |
| 4,682,606 A | 7/1987 | DeCaprio |
| 4,799,495 A | 1/1989 | Hawkins et al. |
| 4,800,899 A | 1/1989 | Elliott |
| 4,869,259 A | 9/1989 | Elkins |
| 4,925,445 A | 5/1990 | Sakamoto et al. |
| 4,966,583 A | 10/1990 | Debbas |
| 5,011,473 A | 4/1991 | Gatturna |
| 5,018,530 A | 5/1991 | Rank et al. |
| 5,059,197 A | 10/1991 | Urie et al. |
| 5,067,957 A | 11/1991 | Jervis |
| 5,122,136 A | 6/1992 | Guglielmi et al. |
| 5,158,084 A | 10/1992 | Ghiatas |
| 5,183,463 A | 2/1993 | Debbas |
| 5,190,054 A | 3/1993 | Fetter et al. |
| 5,190,546 A | 3/1993 | Jervis |
| 5,197,482 A | 3/1993 | Rank et al. |
| 5,205,829 A | 4/1993 | Lituchy |
| 5,217,027 A | 6/1993 | Hermens |
| 5,221,269 A | 6/1993 | Miller et al. |
| 5,246,438 A | 9/1993 | Langberg |
| 5,282,845 A | 2/1994 | Bush et al. |
| 5,300,068 A | 4/1994 | Rosar et al. |
| 5,301,682 A | 4/1994 | Debbas |
| 5,350,419 A | 9/1994 | Bendel et al. |
| 5,353,804 A | 10/1994 | Kornberg et al. |
| 5,370,644 A | 12/1994 | Langberg |
| 5,409,004 A | 4/1995 | Sloan |
| 5,462,062 A | 10/1995 | Rubinstein et al. |
| 5,472,441 A | 12/1995 | Edwards et al. |
| 5,486,183 A | 1/1996 | Middleman et al. |
| 5,488,958 A | 2/1996 | Topel et al. |
| 5,507,743 A | 4/1996 | Edwards et al. |
| 5,520,684 A | 5/1996 | Imran |
| 5,536,267 A | 7/1996 | Edwards et al. |
| 5,540,683 A | 7/1996 | Ichikawa et al. |
| 5,556,410 A | 9/1996 | Mittermeir et al. |
| 5,558,673 A | 9/1996 | Edwards et al. |
| 5,672,173 A | 9/1997 | Gough et al. |
| 5,672,174 A | 9/1997 | Gough et al. |
| 5,683,384 A | 11/1997 | Gough et al. |
| 5,685,853 A | 11/1997 | Bonnet |
| 5,700,243 A | 12/1997 | Narciso, Jr. |
| 5,709,697 A | 1/1998 | Ratcliff et al. |
| 5,720,718 A * | 2/1998 | Rosen et al. ............. 604/22 |
| 5,735,847 A | 4/1998 | Gough et al. |
| 5,741,225 A | 4/1998 | Lax et al. |
| 5,749,887 A | 5/1998 | Heske et al. |
| 5,776,176 A | 7/1998 | Rudie |
| 5,794,626 A | 8/1998 | Kieturakis |
| 5,795,308 A | 8/1998 | Russin |
| 5,800,484 A | 9/1998 | Gough et al. |
| 5,807,339 A | 9/1998 | Bostrom et al. |
| 5,810,804 A | 9/1998 | Gough et al. |
| 5,853,366 A | 12/1998 | Dowlatshahi |
| 5,855,576 A | 1/1999 | LeVeen et al. |
| 5,863,290 A | 1/1999 | Gough et al. |
| 5,879,357 A | 3/1999 | Heaton et al. |
| 5,882,316 A | 3/1999 | Chu et al. |
| 5,897,554 A | 4/1999 | Chia et al. |
| 5,902,310 A | 5/1999 | Foerster et al. |
| 5,904,690 A | 5/1999 | Middleman et al. |
| 5,904,709 A | 5/1999 | Arndt et al. |
| 5,938,692 A | 8/1999 | Rudie |
| 5,941,890 A | 8/1999 | Voegele et al. |
| 5,954,655 A | 9/1999 | Hussman |
| 5,954,719 A | 9/1999 | Chen et al. |
| 5,957,969 A | 9/1999 | Warner et al. |
| 5,974,343 A | 10/1999 | Brevard et al. |
| 5,980,563 A | 11/1999 | Tu et al. |
| 5,989,265 A | 11/1999 | Bouquet De La Joliniere et al. |
| 6,007,495 A | 12/1999 | Matula |
| 6,016,811 A | 1/2000 | Knopp et al. |
| 6,019,757 A | 2/2000 | Scheldrup |
| 6,022,362 A | 2/2000 | Lee et al. |
| 6,027,524 A | 2/2000 | Petit |
| 6,032,078 A | 2/2000 | Rudie |
| 6,039,735 A | 3/2000 | Greep |
| 6,050,954 A | 4/2000 | Mittermeier |
| 6,051,008 A | 4/2000 | Saadat et al. |
| 6,053,876 A | 4/2000 | Fisher |
| 6,053,925 A | 4/2000 | Barnhart |
| 6,073,051 A | 6/2000 | Sharkey et al. |
| 6,080,113 A | 6/2000 | Heneveld et al. |
| 6,080,114 A | 6/2000 | Russin |
| 6,080,150 A | 6/2000 | Gough |
| 6,097,985 A | 8/2000 | Kasevich et al. |
| 6,106,518 A | 8/2000 | Wittenberger et al. |
| 6,134,476 A | 10/2000 | Arndt et al. |
| 6,146,379 A | 11/2000 | Fleischman et al. |
| 6,146,657 A | 11/2000 | Unger et al. |
| 6,181,970 B1 | 1/2001 | Kasevich |
| 6,217,528 B1 | 4/2001 | Koblish et al. |
| 6,233,490 B1 | 5/2001 | Kasevich |
| 6,245,064 B1 | 6/2001 | Lesh et al. |
| 6,245,318 B1 | 6/2001 | Klibanov et al. |
| 6,251,128 B1 | 6/2001 | Knopp et al. |
| 6,275,738 B1 | 8/2001 | Kasevich et al. |
| 6,290,715 B1 | 9/2001 | Sharkey et al. |
| 6,306,132 B1 | 10/2001 | Moorman et al. |
| 6,325,796 B1 | 12/2001 | Berube et al. |
| 6,355,033 B1 | 3/2002 | Moorman et al. |
| 6,405,733 B1 | 6/2002 | Fogarty et al. |
| 2001/0001819 A1 | 5/2001 | Lee et al. |
| 2001/0051131 A1 | 12/2001 | Unger |
| 2002/0059938 A1 | 5/2002 | Fogarty et al. |
| 2002/0087151 A1 | 7/2002 | Mody et al. |

FOREIGN PATENT DOCUMENTS

| | | |
|---|---|---|
| WO | WO 00/12009 | 3/2000 |
| WO | WO 00/12010 | 3/2000 |
| WO | WO 00/13602 | 3/2000 |
| WO | WO 00/16697 | 3/2000 |
| WO | WO 00/24320 | 5/2000 |
| WO | WO 00/28913 | 5/2000 |
| WO | WO 00/30531 | 6/2000 |
| WO | WO 00/33743 | 6/2000 |
| WO | WO 01/05317 | 1/2001 |
| WO | WO 01/05320 | 1/2001 |
| WO | WO 01/60235 | 8/2001 |

OTHER PUBLICATIONS

Anonymous. (1999). *Auto Suture MIBB Site Marker: Single Use Chip Applier, United States Surgical* (Product instructions), 2 pages.

Anonymous. (1999). *MIBB Site Marker, United States Surgical* (Sales brochure), 4 pages.

Anonymous. (2001). *Disposable Chiba Biopsy Needles and Trays*, Biopsy and Special Purpose Needles *Cook Diagnostic and Interventional Products Catalog* (Products list), 4 pages.

Anonymous. *Ariadne's Thread ™ Repositionable Breast Localisation Needle*, (Product Information), one page (date not known).

Anonymous. *Blunt Tubes with Finished Ends. Pointed Cannula, Popper & Sons Biomedical Instrument Division*, (Products Price List), one page (date not known).

Anonymous. *Ground Cannulae, ISPG*, New Milford, CT, (Advertisement) 1 page (date not known).

Chou, C.K. (1995). "Radiofrequency Hyperthermia in Cancer Therapy," Chapter 94 *In Biologic Effects of Nonionizing Electromagnetic Fields*. CRC Press, Inc. pp. 1424–1428.

Gennari, R. et al. (Jun. 2000). "Use of Technetium–99m–Labeled Colloid Albumin for Preoperative and Intrapoerative Localization of Nonpalpable Breast Lesions," *J. Am. Coll. Surg*. 190(6):692–699.

Kopans, D.B. et al. (Nov. 1985). "Spring Hookwire Breast Lesion Localizer: Use with Rigid–Compression. Mammographic Systems," *Radiology* 157(2):537–538.

MDTECH product literature. (Mar., 2000). "D Wire": product description, 1 page.

MDTECH product literature. (Dec., 1999). "FlexStrand": product description, 1 page.

Mullan, B.F. et al. (May, 1999). "Lung Nodules: Improved Wire for CT–Guided Localization," *Radiology* 211:561–565.

Urologix, Inc.—Medical Professionals: Targis™ Technology "Overcoming the Challenge" located at: <http://www.urologix.com/medical/technology.html> visited on Apr. 27, 2001. (Three pages.)

Urrutia et al. (1988). "Retractable–Barb Needle for Breast Lesion Localization: Use in 60 Cases," *Radiology* 169(3):845–847.

\* cited by examiner

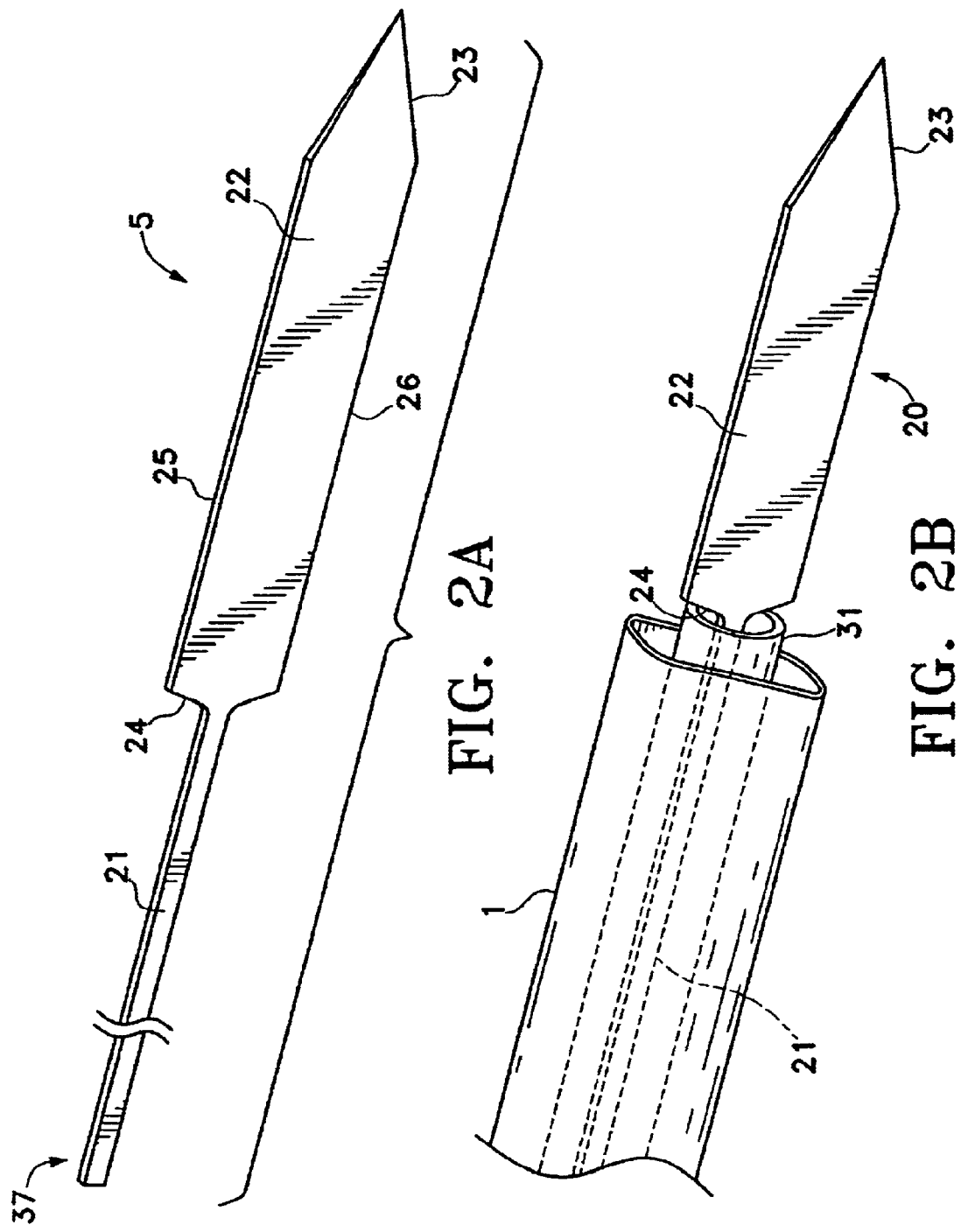

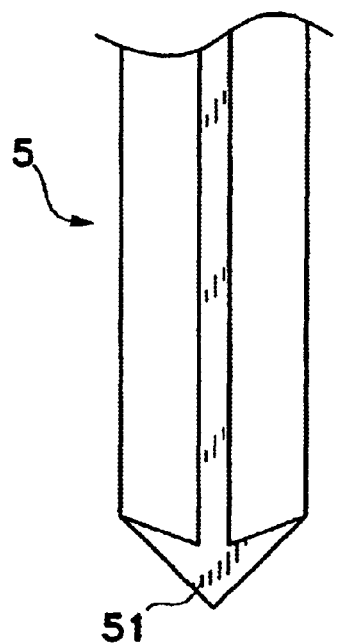
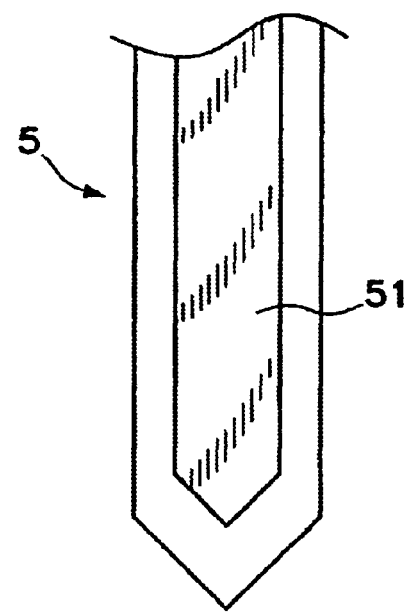
FIG. 7A    FIG. 7B
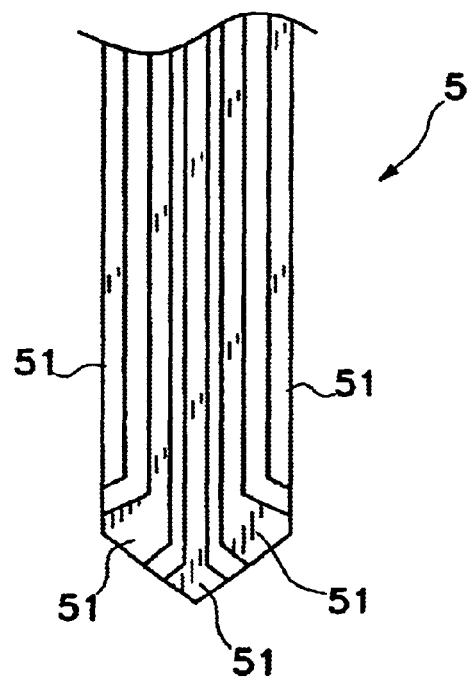
FIG. 8

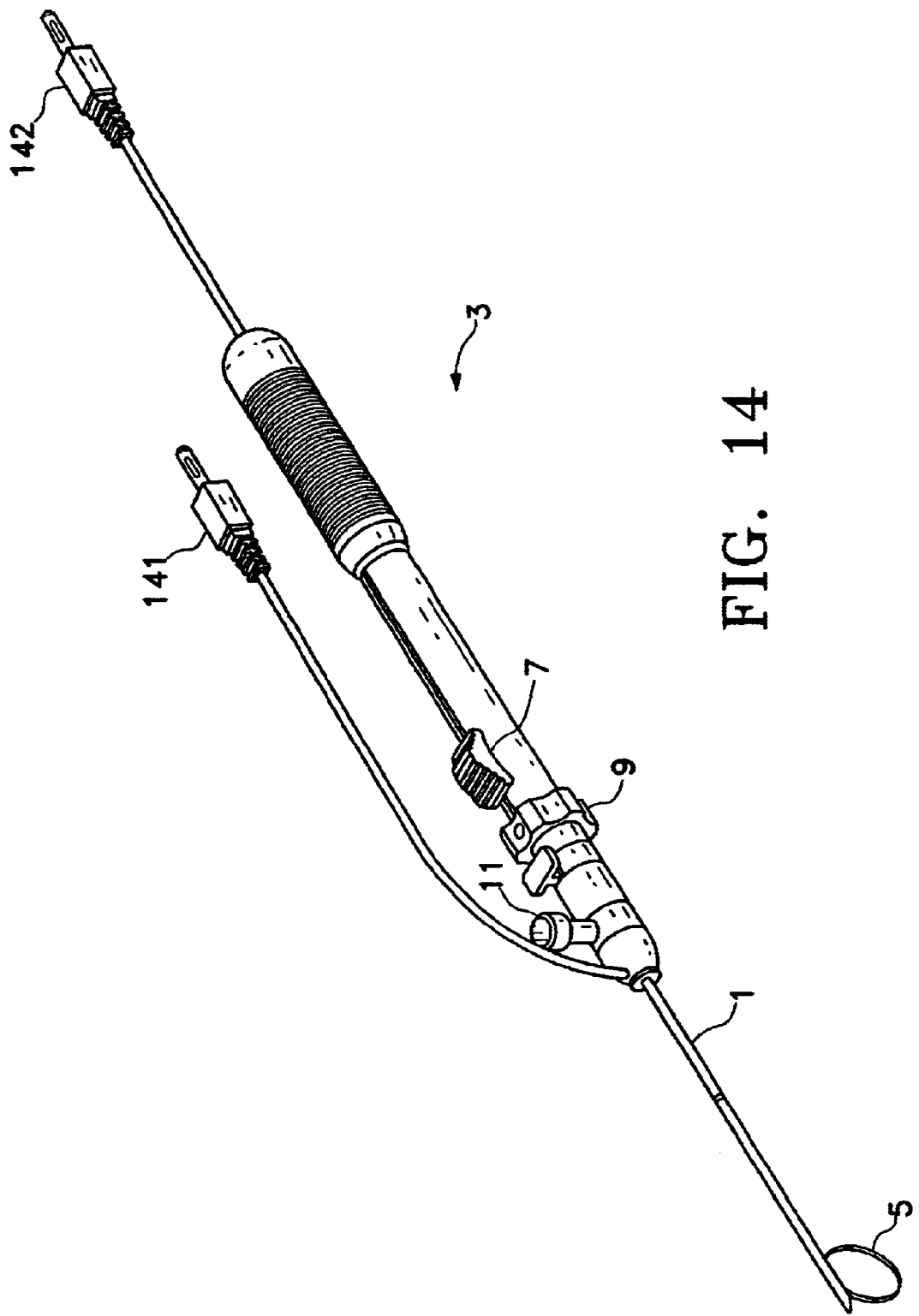

LOCALIZATION ELEMENT WITH ENERGIZED TIP

CROSS-REFERENCE TO RELATED APPLICATIONS

This application is claiming the benefit of priority to U.S. provisional application Ser. No. 60/373,190 filed on Apr. 16, 2002, and is related to co-pending U.S. patent application Ser. No. 10/272,314 entitled "Microwave Antenna Having A Curved Configuration" filed Oct. 15, 2002, and each of which is incorporated herein by reference in its entirety.

FIELD OF THE INVENTION

This invention relates generally to tissue-localizing devices and methods for their deployment and excision. More particularly, this invention relates to an improved tissue localizing device having an electrically energized locator element with ability to fixedly yet removably bound a tissue volume containing a region of interest, such as a nonpalpable lesion, foreign object, or tumor, preferably but not necessarily without penetrating that tissue volume. This invention also more particularly relates to methods for deploying that device and removing it with an enclosed and intact tissue volume.

BACKGROUND

Despite the advances made in technologies such as medical imaging to assist the physician in early stage diagnosis and treatment of patients with possible atypical tissue such as cancer, it is still often necessary to sample difficult-to-reliably-reach organ or tissue lesions by biopsy to confirm the presence or absence of abnormalities or disease.

One disease for which biopsy is a critical tool is breast cancer. This affliction is responsible for 18% of all cancer deaths in women and is the leading cause of death among women aged 40 to 55.

In the detection and treatment of breast cancer, there are two general classes of biopsy: the minimally invasive percutaneous biopsy and the more invasive surgical, or "open", biopsy.

In the detection and treatment of breast cancer, there are two general classes of biopsy: the minimally invasive percutaneous biopsy and the more invasive surgical, or "open", biopsy.

Percutaneous biopsies include the use of fine needles or larger diameter core needles. They may be used on palpable lesions or under stereotactic x-ray, ultrasonic, or other guidance techniques for nonpalpable lesions and microcalcifications (which are often precursors to metastatic cell growth). In the fine needle biopsy, a physician inserts a small needle directly into the lesion and obtains a few cells with a syringe. Not only does this technique require multiple samples, but each sample is difficult for the cytologist to analyze as the specimen cells are isolated outside the context of healthy surrounding tissue.

Larger samples may be removed via a core biopsy. This class of procedures is typically performed under stereotactic x-ray guidance in which a needle is inserted into the tissue to drill a core that is removed via vacuum aspiration, etc. Typically four to five samples are taken from the body. Examples of such stereotactic biopsy methods include the MAMMOTOME vacuum aspiration system by Johnson & Johnson of New Brunswick, N.J., the ABBI system by United States Surgical Corporation, Norwalk, Conn, and the SITESELECT system by Imagyn, Inc. of Irvine, Calif.

Open biopsies are advisable when suspicious lumps should be removed in their entirety or when core needle biopsies do not render sufficient information about the nature of the lesion. One such type of open biopsy is the wire localization biopsy.

After multiple mammograms are taken of the breast, the images are analyzed by a computer to determine the location of the suspect lesion in three dimensions. Next, after a local anesthetic is administered, a radiologist inserts a small needle into the breast and passes the needle through the suspect tissue. The radiologist then passes a wire with a hook on its end through the needle and positions the hook so that the end of the wire is distal to the suspect tissue. A final image is taken of the lesion with the accompanying wire in place, and the radiologist marks the film with a grease pencil to indicate the x-ray indicators of a suspicious lesion that should be removed. The wire is left in the tissue and the patient is taken to the operating room, sometimes hours later, where the suspect tissue is removed by a surgeon. The sample is sent to a radiologist to determine, via an x-ray examination, if the sample contains the indicators such as microcalcifications and if the sample size and border are adequate to confirm the removal of all suspicious tissue.

Examples of such wire markers are well known in the art. See, e.g., the following patents, each of which is incorporated herein by reference: U.S. Pat. No. 5,158,084 to Ghiatas, U.S. Pat. No. 5,409,004 to Sloan, U.S. Pat. No. 5,059,197 to Urie et al., U.S. Pat. No. 5,197,482 to Rank, U.S. Pat. No. 5,221,269 to Miller et al., and U.S. Pat. No. 4,592,356 to Gutierrez. Other devices such as that described in U.S. Pat. No. 5,989,265 to Bouquet De La Joliniere et al. and U.S. Pat. No. 5,709,697 to Ratcliff et al., each incorporated herein by reference, are directed to similar devices.

Despite the advantages of wire localization techniques to locate the suspect tissue for the surgeon, they have a number of severe limitations.

Such wires are often inaccurately placed and they cannot be removed except by surgical excision. For these reasons, the radiologist must mark the x-ray film or prepare notations providing instructions to the surgeon on how to find the lesion as a backup to confirm the proper location of the needle.

Because the distal tip of the wire might have been placed anywhere from the very center of the lesion to quite some distance away from the lesion, the surgeon must guide a scalpel along the wire and rely upon the skill of the radiologist and the marked x-ray film in the excision procedure. Even if the wire has been properly placed in the lesion and the x-ray film clearly shows the lesion boundary or margin, the surgeon often cannot see the tip of the wire (given the surrounding tissue) so she must remove a larger portion of tissue than is necessary to ensure proper excision.

If the lesion is not found at the end of the wire, the surgeon ends up cutting or removing non-afflicted tissue without removing the lesion. Also, if the tip of the wire penetrates the lesion, the surgeon may sever the lesion in cutting through the tissue along the wire to reach its end. In the latter case, a re-excision may be necessary to remove the entire lesion. Over twenty-five percent of wire localization procedures require re-excision. Post-excision re-imaging is almost always performed prior to closing the surgical field to ensure that the targeted tissue volume containing the suspect lesion is removed.

When marking lesions in the breast, two paddles are typically used to compress and stabilize the breast for placement of the wire. Upon release of the breast from compression, the wire marker can dislodge or migrate to another position away from the suspect tissue. It may also migrate while the patient awaits surgery. In addition, the fact that the breast is in an uncompressed state for the excision procedure renders a different view of the lesion with respect to the healthy tissue.

Various tissue localization systems have been developed to minimize inadvertent migration of the wire by configuring the wire with a bend or hook, such as Ghiatas et al., discussed above, U.S. Pat. No. 5,011,473 to Gatturna, and the MAMMALOK needle/wire localizer sold by Mitek Surgical Products, Inc., Dedham, Mass. Even if a wire does not migrate after placement, the surgeon cannot determine the shortest path to the lesion; rather, the surgeon must always follow the wire, which is rarely the more cosmetically desirable path to the lesion (such as a circumareolar approach).

Because the distal tip of the wire is often placed in the center of the suspect tissue, a problem known as "track seeding" can occur in which possible cancerous or precancerous cells are disturbed by the wire and are distributed to unaffected tissue during the procedure.

Aside from the above concerns, the use of a localization wire marker presents logistical problems. After placement, the wire protrudes from the body. It is almost always necessary for the patient to proceed with the surgical removal of the lesion immediately after wire placement to minimize the chance of infection, wire breakage or disturbance, etc. However, delays between placement of the wire and eventual excision often can exceed several hours.

Furthermore, conventional tissue locators tend to be difficult to deploy in areas where there is scar tissue, calcified tissues, or particularly dense tissues. The locator element or wiring that is inserted into the tissue tends to be blocked by scar tissue and other hardened tissues. It is highly desirable to have an effective means to facilitate the insertion of a locator element by minimizing resistance due to calcified tissue and other hardened tissues.

What is needed is a tissue-locating device that may be smoothly inserted into the subject to surround a volume of interested tissue with minimal effort and maximum precision. Such a device should reliably define the border of the volume of tissue to be removed without the risk of self or inadvertent migration. The device should also provide a surface against which the surgeon may reliably cut when excising the tissue. Furthermore, a need remains to improve the interaction between the radiologist and surgeon, eliminate the need for post-excision x-rays and re-excision, reduce the overall time for the procedure, and allow a surgeon to select the shortest or most cosmetically desirable path to the suspect tissue.

SUMMARY OF THE INVENTION

The present invention relates to a tissue-localizing device with an energized locator element and methods for its use. The tissue-localizing device includes a locator element adapted to penetrate tissue so that the distal portion of the locator element forms at least a partial loop that defines a volume of tissue when the locator element is deployed in a mammalian body. The locator element, when deployed, may define a volume of tissue for subsequent excision and contains a target region that may contain a lesion, foreign object, one or more microcalcifications, or a palpable or nonpalpable mass. This tissue volume is substantially bounded but preferably not penetrated by the locator element. The locator element may be adapted to form a partial or complete loop around a target region having a diameter as small as three millimeter. It is preferable that the loop formed by the locator element has a diameter in the range of about three millimeter to about ten centimeter. It is even more preferable that the diameter of the loop be within the range of about five millimeter to about five centimeter. When deployed, manipulation of a proximal portion of the locator element may result in a corresponding direct or proportional manipulation of the tissue volume it bounds.

The conductive locator element may be configured for delivering a current or an electromagnetic field depending on the particular application. For example, the locator element may be configured as an electrode to carry alternating current of various radio frequencies. In this application, a second electrode or conductive member may be adapted to complete the current loop so that current may flow from the locator element to this secondary electrode or conductive member. Alternatively, the locator element may be configured as an antenna to deliver electromagnetic field to the localized tissue. The electromagnetic field is generated when an alternating current is inputted to the antenna.

It is preferable that alternating current within the radio frequency (RF) spectrum is used to energize the locator element or a conductive region on the locator element. It is more preferable that the energizing current carries a frequency or frequencies within the range of about three kilohertz to about three hundred gigahertz. The power supply may have an alternating current output power within a range of zero to about four hundred watts. For RF ablation applications, it is more preferable that the primary RF frequency is within about ten kilohertz to about one hundred megahertz. It is even more preferable that in RF ablation application that the primary RF frequency be within about one hundred kilohertz to about one megahertz. For ultrasound applications, it is more preferable that the locator element is energized with a current carrying at least a frequency within the range of about ten kilohertz to about fifty megahertz. It is even more preferable that in ultrasound application the frequency be within the range of about five hundred kilohertz to about ten megahertz. For microwave applications, it is more preferable that the locator element is energized with a current carrying at least a frequency within the range of about one hundred megahertz to about three hundred gigahertz. It is even more preferable that in microwave application the frequency be within the range of about three hundred megahertz to about three gigahertz.

The RF energized locator element may be used to facilitate the deployment of the locator element. Alternatively, the energized locator element may be used to deliver RF current or RF electromagnetic wave to a localized region of tissue for therapeutic or medical intervention purposes.

Preferably the locator element is at least partially radiopaque ribbon with one or more optional cutting surfaces. The locator element also preferably exhibits shape memory characteristics. Alternatively, the locator element may be plastically deformed to take an arcuate or curvilinear shape during deployment through a die.

The locator element is adapted to penetrate tissue so that at least part of the distal portion of the locator element forms a partial loop that defines a volume of tissue. The locator element defines a volume of tissue that may be subsequently excised along the boundary defined by the locator element.

The locator element is preferably electric conductive. Various metals and metal alloys that are highly conductive may be used to construct the locator element. The locator element may also be at least partially electrically insulated with a coating of insulating material, such as a polymer coating, on one or more sides of the locator element. The insulating layer may be biocompatible plastics such as parylene, polyethylene, polypropylene, polyvinylchloride (PVC), ethylvinylacetate (EVA), polyethyleneterephthalate (PET), polyurethanes, polycarbonates, polyamide (such as the Nylons), silicone elastomers, fluoropolymers (such as Teflon™), and their mixtures and block or random copolymers may be applied as an insulating layer and/or as a protective coating. This insulative material may have a low coefficient of friction for ease of entry into the tissue. Alternatively, the electric insulation may also be achieved through placement of a heat-shrink tubing over the locator element. Preferably the distal end of the locator element is exposed to provide a path for delivery of electric energy to the tissue.

Alternatively, the locator element may be constructed with a non-conductive material, such as super elastic polymer, and a conductive member is then adapted to the body of the locator element to provide the means for electric conduction. Conductive regions may also be established on a locator element through electroplating, electrodepostition or plasma deposition of conductive materials, such as copper, chromium, silver or gold.

Alternatively, the locator element has two or more conductive regions. In one variation, the plurality of conductive regions is constructed on the surface of the locator element through adaptation of two independent conductive members, such as metal wires with high conductivity, to the locator element. It may also be possible to fabricate the two electrodes on the surface of the locator element through deposition of conductive materials, such as copper, chrome, silver, gold or metal alloys, on the surface of the locator element. Two or more surfaces that are electrically isolated from each other may be deposited on the surface of the conductor element through plasma thin film deposition, electroplating or electrodeposition. Alternatively, a plurality of electrodes may be fabricated on the locator element through placement of multiple layers of conductive materials that are electrically insulated from each other. For example, on top of a locator element constructed of metal alloy, an insulating layer, such as polyamide or other polymers with low conductivity, maybe deposited on its surface, and a layer of conductive material may be deposited on top of the insulating material to serve as the second electrode. A second layer of polymer may be deposited on top of the conductive layer to alter the amount of the conductive area exposed. If necessary, additional layers of conductive materials and polymer may be deposited to create additional electrodes as needed. The independent conductive regions may be selectively implemented as the active and return electrodes in a bipolar electric energizing configuration.

In another variation, one or more electric conductive member may be adapted or coupled to the locator element. If the locator element is also conductive, an insulating layer may be provided to separate the conducting member from the locator element. The conductive member may be comprised of metal wires or electrodes, metal alloy wires or electrodes, and other electric conductive wiring and medium well known to one skilled in the art.

The tissue-localizing device may also include a sleeve that is placed over the locator element. The locator element is slidably positioned within the lumen of the sleeve. The sleeve may be used to penetrate the target tissue. The sleeve may be flexible, semi-flexible or rigid depending on the particular application. Alternatively, the sleeve may comprise a cannula. The distal end of the sleeve may have a sharp edge to facilitate penetration of the tissue.

A locking mechanism may also be provided to temporarily secure the position of the locator element relative to the sleeve. When the locator element is secured by the locking mechanism the sleeve and the locking mechanism may be advanced into the tissue as a single unit.

The sleeve may also be electric conductive. For example, the sleeve may be comprised of a metal cannula. An insulating layer may be placed over the sleeve exposing only the distal end of the sleeve. Alternatively, metal deposition techniques well known to one skilled in the art may be applied to establish a conductive region on the sleeve. It is preferable, but not necessary, that the conductive region be on the distal end of the sleeve. The conductive sleeve may also be energized to facilitate the penetration of the sleeve into the tissue. Alternatively, the conductive sleeve may provide a return pathway for electric current in a bipolar electric configuration.

The sleeve may additionally comprise a cold forming die at the distal end of the sleeve that is adapted to plastically deform the locator element into an arcuate shape. The die may include a reverse curve and a positive curve for shaping the locator element, and it may also comprise an axially adjustable upper portion connected to a lower portion.

A power supply may be connected to the locator element for delivering electric energy to the conducting surface on the locator element. The power supply may be able to deliver a current with a particular frequency within the range from about three kilohertz to about three hundred gigahertz. Alternatively the power supply may have a variable current output with a frequency range within the three kilohertz to three hundred gigahertz range. Various RF, microwave, and ultrasound generators well known to one skilled in the art may be adapted to provide the electric energy to the locator element. In another variation, the power supply may deliver a DC current to the to the locator element.

The power supply and the tissue-localizing device may be configured to deliver electric energy to tissue. The system may be specifically configured for delivering RF ablation current, microwave energy, ultrasound energy, and other electric energy that are well known to one skilled in the art. As described above, the electric energy is preferably delivered to the target region as an electric current, but it may also be delivered to the target region as an electromagnetic wave.

The delivery of energy may be achieved through monopolar or bipolar configurations. In a monopolar configuration, the locator element preferably serves as the primary electrode deliverying the electric energy. In applications where the primary electrode is used to delivery a current to the tissue, a secondary electrode or conductive pad may be place on the subject to provide a return path for the current to flow back to the power supply. In an alternative arrangement, the locator element may serve as the secondary or ground electrode, and a separate electrode or conductor is placed at a separate location on the subject to complete the electric loop.

The monoplar configuration may be achieved through implementation of a locator element with an electric conductive surface. In one variation, the power supply is electrically connected to a conductive path that connects to the conductive surface on the locator element. An electric conductive pad is secured to the surface of the subject's body and a separate electric conductive path connects the pad to the negative or ground connection on the power supply to complete the electric current loop.

In a monopolar configuration, it may also be possible to direct the current down the sleeve of the tissue-localizing device to facilitate the insertion of the sleeve into the tissue. Once the sleeve is in position, a current may be directed down the locator element to facilitate the deployment of the locator element. In one variation, the same current source is used to charge the sleeve and the locator element. A current switch may be incorporated to selectively direct current down the sleeve and/or the locator element.

In the bipolar configuration, it is preferable that the locator element serve as the primary electrode and the sleeve serve as the secondary electrode. It is also possible to use a locator element with two or more separate conductive regions. In such a case, both the positive and negative electrodes for the bipolar system may be located on the locator element.

The power supply may be integrated with the tissue-localizing device as one unit or it may stand as a separate unit connected to the tissue-localizing device. The power supply may deliver DC and/or AC current depending on the particular application. Integrated circuit based switching and controlling circuits may be implemented to manufacture a miniature power control unit that can easily be integrated into a handle that is attached to the sleeve and the locator element. In some applications, a separate unit containing the power supply and control circuit may be preferable in order to minimize the production cost of the system or to implement a more sophisticated feed back control mechanism that is capable of monitoring physiological changes and modulate the ablation current during the insertion of the tissue-localizing device.

A temperature sensor may also be adapted or coupled to the tissue-localizing device for monitoring local tissue temperature fluctuation. This may be particularly useful in applications where RF energy is used for ablating tissue around the locator element. The temperature sensor allows for monitoring of local tissue temperature to guard against over heating of tissue. A close loop control mechanism, such as a feedback controller with a microprocessor, may be implemented for controlling the delivery of RF energy to the target tissue based on temperature measured by the temperature sensor.

The temperature sensor may be coupled or adapted to the locator element, or alternatively coupled or adapted to the sleeve of the tissue-localizing device. Miniature sensors well known to one skill in the art and suitable for this particular in vivo application may also be used. For example, thermal couples, thermistors, and various semiconductor based temperature sensors may be implemented on the tissue-localizing device.

This invention is also a method for placing a removable locator element in tissue. This method is accomplished by inserting a sleeve containing a locator element slideably positioned within a lumen of the sleeve at a position adjacent the targeted tissue, and advancing a locator element through a distal end of the sleeve and penetrating tissue so that at least a portion of the locator element forms a partial loop around the target tissue. The deployed locator element defines a volume of tissue for subsequent treatment or excision. The tissue volume will contain a target region that is substantially bounded but not penetrated by the locator element.

The sleeve and/or the locator element may be energized with RF energy to facilitate the penetration of the sleeve/locator-element unit into the tissue. The RF energy may be delivered simultaneously while the sleeve/locator-element is being advanced into the tissue, or alternately by energizing the locator element in between intermitted pressure applied to advance the locator element into the tissue.

Alternatively, the invention is a method for excising a volume of tissue that comprises advancing a locator element with the assistance of RF energy through tissue to define a volume of tissue to be excised, and cutting tissue substantially along a surface of the locator element immediately adjacent the tissue volume. Rotation of the locator element or elements through an angular displacement, to facilitate cutting through tissue to remove the tissue volume is also feasible. RF energy may also be applied, intermittently or continuously, to the locator element to facilitate the excision of the target tissue.

Preferably, the device is palpable when in position around the tissue volume. Tissue may be penetrated through any excision path to the tissue volume as the surgeon sees fit. For instance, the surgeon may cut down along the locator element extension wire, or, when the device is disposed in breast tissue, circumareolarly.

The locator element may be proximally withdrawn from the tissue after it is advanced to define the tissue border for eventual re-advancement through the distal end of the deployment sleeve or complete removal from the body.

The locator element may be placed under x-ray guidance, stereotactic x-ray guidance, ultrasonic guidance, magnetic resonance imaging guidance, and the like. Target region visibility may be enhanced by, e.g., the placement or injection of an echogenic substance, such as collagen, hydrogels, microspheres, microbbules, or other like biocompatible materials, or by the injection of air or other biocompatible gases or contrast agents.

The tissue-localizing device with an energizable locator element may also be utilized for local activation of drug, medication or chemicals. An inactivated chemical may be injected into the body of the subject. The drug diffuses in the subject's body through the circulatory system. The locator element is deployed around the target tissue. Delivery of RF energy, microwave or ultrasound may activate the chemical locally around the target region. The chemicals may be activated by direct RF energy due to the chemicals entering the RF energy field, or it may be activated due to the elevated temperature in the local tissue exposed to the RF energy. Alternatively, it may also be possible to activate drugs or chemicals with RF current.

Variations of the invention may also include a tissue locator element pusher assembly. The pusher assembly is adapted to the sleeve and the locator element. A pusher within the pusher assembly may be adapted to control the sliding action of the locator element along the lumen of the sleeve. An adjustable fastener for slidably fixing a portion of a tissue locator element to the pusher may also be included. A deployment fixture may be detachably affixed to a distal end of the locator element. The locator element may be released and separated from the pusher assembly.

Alternatively, the tissue locator element pusher assembly may include a housing having a lumen, a pusher having a pusher lumen slidably disposed in the housing lumen, a tissue locator element at least partially disposed in the pusher lumen, and a delivery tube or sleeve having an optional sharpened distal tip and affixed to the housing. The delivery tube or sleeve has a lumen adapted for slidably receiving the pusher and the tissue locator element.

Still further, the tissue locator element pusher assembly may include a housing having a proximal end, a distal end, a central housing lumen, and at least one longitudinal slot in communication with the housing lumen, and a pusher slidably disposed in the housing lumen. The pusher may have a pusher lumen and an adjustable fastener for slidably fixing a portion of a tissue locator element to the pusher, a control lever affixed to the pusher and extending at least partially through the housing slot, and a tissue locator element at least partially disposed in the pusher lumen. A delivery tube or sleeve may have a lumen adapted for slidably receiving the pusher, and the locator element may be disposed on the distal end of the housing in communication with the housing lumen.

Further, this pusher assembly may be configured so that axial movement of the control lever will result in a corresponding axial movement of the pusher and the locator element. In this way, the locator element will reversibly extend through an aperture in a distal end of the delivery tube. The assembly may also be set up so that sufficient axial movement of the control lever may cause it to engage a detent disposed in the housing, prohibiting substantial further axial movement of the control lever. The engagement of the control lever and the detent may be configured to correlate to an extension of the locator element shoulder through the delivery tube distal end aperture. The assembly may further be set up so that just prior to engaging the detent, tactile or other feedback is provided to indicate that the engagement point is about to be reached.

Furthermore, the tissue localizing system may include electronic controller that is adapted to modulate the RF current delivered to the locator element. The controller may be integrated with the pusher assembly or it may be integrated with the power supply. Alternatively, the controller may be a separate unit connected to the power supply and the pusher assembly. The controller may be adapted to energize the locator element when a pressure is applied to advance the locator element forward. Alternatively, the power controller may be adapted to respond to a control switch that is located on the pusher assembly or as a separate unit that is in communication with the controller. In another variation, the controller may only energize the locator element when the locator element experiences a resistance that is above a predefined threshold during the deployment process.

The sleeve of the tissue-localizing device may be adapted for delivery of fluids, chemicals or drug into the tissue. A delivery port and a fluid communication channel connecting the port to the lumen of the sleeve may be integrated into the pusher assembly to facilitate the delivering fluid to the tissue via the sleeve of the tissue-localizing device.

Although the tissue locator element is primarily intended to mark a volume of tissue without penetrating it, the tissue locator element may be used as a tissue localization wire in which at least a portion of a tissue volume (which may or may not include a lesion) is penetrated to mark it for later excision.

BRIEF DESCRIPTION OF THE DRAWINGS

The foregoing and other objects, features and advantages of the invention will become apparent from the following description of the invention, as illustrated in the accompanying drawings in which reference characters refer to the same parts through out the different views. The drawings are intended for illustrating some of the principles of the invention and are not intended to limit the invention in any way. The drawings are not necessarily to scale, emphasis instead being placed upon illustrating the principles of the invention in a clear manner.

FIG. 2A shows one embodiment of a locator element according to the present invention.

FIG. 2B shows the locator element of FIG. 2A together with a deployment sleeve and a pusher element;

FIG. 7A shows one side of a variation of a locator element according to the present invention with a conductive region on each of the two sides of the locator element;

FIG. 7B shows the corresponding opposite side of the locator element shown in FIG. 7A;

FIG. 8 illustrates another variation of a locator element according to the present invention with a plurality of conductive regions;

FIG. 14 shows a variation of a bipolar RF energized tissue-localizing device according to the present invention.

DETAIL DESCRIPTION OF THE INVENTION

Tissue localizing devices and locator elements having particular use in the present invention can have a variety of shape and configurations, including configuration such as those described in U.S. patent application Ser. No. 09/935,477, filed Aug. 22, 2001, PCT Application Serial No. PCT/US01/05013, filed Feb. 16, 2001, U.S. patent application, Ser. No. 09/699,254, filed Oct. 27, 2000, U.S. patent application Ser. No. 09/613,686, filed Jul. 11, 2000, and U.S. patent application Ser. No. 09/507,361, filed Feb. 18, 2000, each of which is incorporated herein by reference in its entirety. These applications describe in detail various aspects of tissue localizing devices and methods for their deployment and excision.

Figure 1:
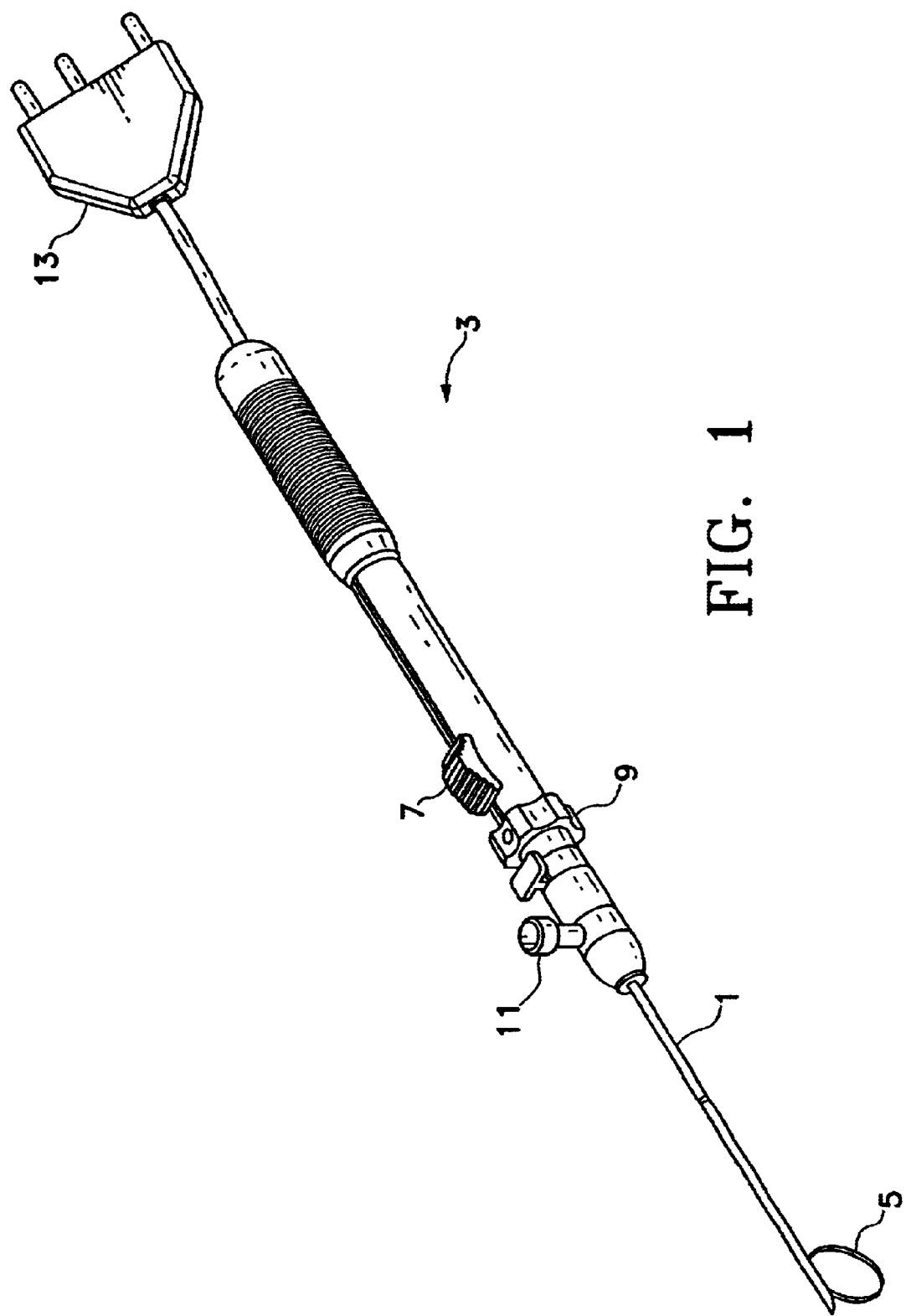
FIG. 1 illustrates a tissue-localizing device according to one variation of the invention with its locator element deployed.

Referring to FIG. 1, a particular variation of a tissue-localizing device according to the present invention is illustrated. The device has a sleeve 1 extending from the pusher assembly 3. The inner surface of the sleeve is preferably, but not necessarily, covered with an insulating liner (not shown). A locator element 5 is slidably located in the lumen of the sleeve. The locator element 5 is shown in the deployed looped position. The locator element is preferably electric conductive. An electric insulating layer May be applied over the locator element. Preferably, the distal end of the locator element is exposed and not covered by the insulating layer. This particular pusher assembly 3 includes a deployment knob 7 inter-linked with the locator element for deploying and retracting the locator element. The pusher assembly 3 may also includes a release ring 9 for detaching the locator element 5 from the pusher assembly 3. A delivery port 11 may also be adapted to the pusher assembly to provide an entry point for delivery of fluids or medication into the lumen of the sleeve 1. A fluid channel (not shown) provides a path from the delivery port 11 to the lumen of the sleeve. The pusher assembly may further include a power cord 13 for connection to a power supply such as a RF generator.

Figure 2C:
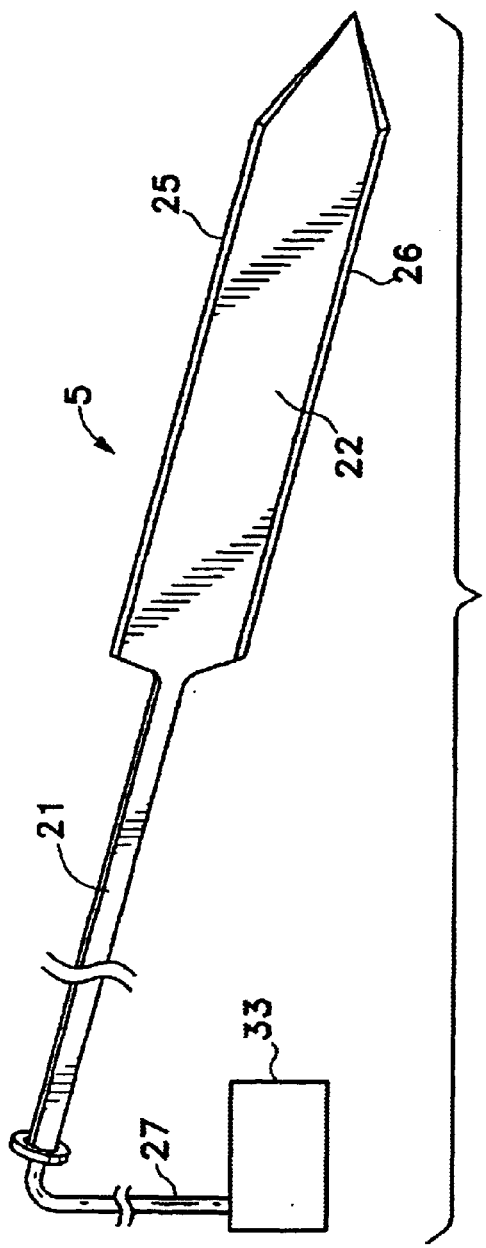
FIG. 2C shows another embodiment of a locator element according to the present invention that is connected to an external energy source.

FIGS. 2A–2E depict various embodiments of the locator element 5. In FIG. 2A, a particularly useful variation of the locator element 5 is shown in perspective as having a straight and flat configuration as it assumes when disposed in the confines of a lumen of a sleeve 1.

A proximal portion 21 of locator element 5, preferably having a smaller cross-sectional area than a distal portion 22 of locator element, is shown. Proximal portion 21 transitions through a radius to distal portion 22 at shoulder 24. Preferably, the entire locator element 5 is a single-piece article having no joints or the like. When a single piece, the proximal portion 21 may be formed by laser or photoetching, traditional, electron-discharge or water-jet machining, cutting, or other techniques to reduce its cross-sectional area relative to distal portion 22. We have found that it is particularly desirable, both for manufacturing and for clinical performance, to start with a single wire made of nitinol, spring steel, or the like, and can have round or square or other cross-sectional configurations. The proximal portion 21 of the wire is ground to the desired diameter. The distal portion 22 is then cold rolled to flatten it.

Alternatively, the distal portion can be hot rolled, hot or cold stamped, coined and the like. Then the distal end 23 of the distal portion 22 is ground or otherwise modified to form a pointed tip and/or one or more edges 25, 26 may be sharpened as described below. In another variation, the distal tip may be kept blunt. A blunt tip may improve physician safety and may also to minimize trauma to the inside of the delivery cannula or sleeve during deployment (e.g. reduce skiving or other resultant scratching from the sharp tip against the inside of the cannula). In some cases, it may be desirable to heat treat the material following the rolling or stamping process and prior to forming the curve. The material may be partially stress relieved to make it less brittle to allow it to take the shape of the curve without breaking; in the case of nitinol, it is only partially annealed to a point at which it still maintains its superelastic properties. Alternatively, for some materials and configurations, the proximal portion 21 may be annealed without annealing the distal portion 22 to impart flexibility to only the proximal portion 21.

Alternatively, proximal portion 21 may be a separate article joined to distal portion 22 at shoulder 24 by any appropriate technique, such as soldering, welding, brazing, adhesives, or the like.

Whether the locator element 5 is a single piece or a separate proximal portion 21 joined to distal portion 22, and especially if it is a single piece, it may be desirable to include a strain relief. In the case where the distal portion is not substantially stiffer than the proximal portion, a serpentine or helical strain relief serves to decouple the two portions such that manipulating the proximal end protruding from the body will not substantially dislodge the distal portion or manipulate tissue within the distal portion.

We prefer proximal portion 21 and distal portion 22 to each have a similarly square or rectangular cross-sectional profile, but other profiles such as circular, elliptical, and irregular are also contemplated. The cross-sectional profile of proximal section 21 need not be the same as the cross-sectional profile of distal portion 22. Furthermore, while FIG. 2A shows only a width difference between proximal portion 21 and distal portion 22, these portions may also differ in thickness.

The smaller cross-sectional area of proximal portion 21 compared to the distal portion 22 (as well as any possible differences in material properties when these portions are made from dissimilar materials) reduces the flexural modulus of proximal portion 21 relative to distal portion 22. This affords greater flexibility or bendability to the device to reduce the risk of locator element breakage, injury to others, and tissue trauma when proximal portion extends from the surface of the skin after locator element deployment but before excision. Preferably, proximal portion 21 is flexible enough to be freely and safely manipulated; for instance, proximal portion 21 may be taped or affixed to the patient's skin after deployment. This eliminates the need to have the tissue volume immediately excised, freeing the patient to leave and return for the excision at a later time. Not only does this help to decouple the radiologist from the surgeon, but also it gives the patient more flexibility to do as she pleases and certainly less invasive discomfort.

Shoulder 24, disposed either proximate the distal portion or at the transition of the proximal and distal portions of locator element 5 is a particularly useful optional feature. Shoulder 24 provides an engaging or abutting surface against which the radiologist or surgeon may advance the distal end of the pusher element 31 (see FIG. 2B) so to move locator element 5 out the distal end of deployment tube 1 and into the tissue. Furthermore, it provides a stop against the tissue to prevent locator element 5 from backing out accidentally. Enhancements to this "anchoring" feature of shoulder 24 are discussed below in conjunction with an embodiment of locator element 5 designed for use with a flexible wire, suture, or the like.

Distal portion 22 of locator element 5 is shown in FIGS. 2A and 2B as having a rectangular cross section and a distal end 23 that forms a blade or cutting surface. Alternatively or in addition, one or both of leading edge 25 or trailing edge 26 may form a blade or cutting surface. The particular shape of the distal end 23 and the cutting surface or surfaces are determined by the particular tissue in which the locator element 5 is designed to be placed and other clinical and practical parameters. The configuration of FIG. 2A is but one of many possible variations to provide an efficient advancing surface for moving through tissue.

FIG. 2C shows an alternative configuration in which locator element 5 is connected to a power supply 33, preferably radio frequency (RF) energy, through lead 27. In this embodiment, RF power supply 33 may be a BOVIE (Bovie Medical Corp., Melville, N.Y.) unit or the like to deliver high frequency current to locator element 5. When so energized, the distal portion 22 of the locating element becomes an active electrode that can cut through and optionally cauterize tissue as is well known to those skilled in the art. RF may be used alone to cut through tissue or may be used in conjunction with mechanical cutting means to assist in advancing the distal portion 22 of locating element 5 through tissue.

Power supply 33 may provide other electrical energy forms to locator element 5, or it may also or instead, be a source of mechanical, thermal, acoustic or other type of energy as may be desired. Various other power supply, such as ultrasoud, microwave, and others energy sources well known to one skill in the art may be adapted to provide energy to the locator element.

When providing RF energy, power supply 33 not only aids in advancing the distal portion 22 into position around the tissue volume by cutting through the tissue, it may also be used to aid the surgeon in excising the tissue volume from the body of the patient, for instance, when the energized locator element 5 (or array of elements) is rotated through an angular displacement as will be discussed in greater detail.

In order to facilitate this rotational cutting action, distal portion 22 of locator element may incorporate a leading edge 25, a trailing edge 26, or both, as shown in FIG. 2C. These portions 25 and 26 preferably but not necessarily will have a sharpened profile so to provide a cutting surface for displacing tissue and providing a focus for the high frequency energy. In one variation, only one of these two portions 25 and 26, has a sharpened profile to provide a cutting surface, and the ablation energy may also be focused on this cutting surface to facilitate the rotational cutting action.

Figure 2E:
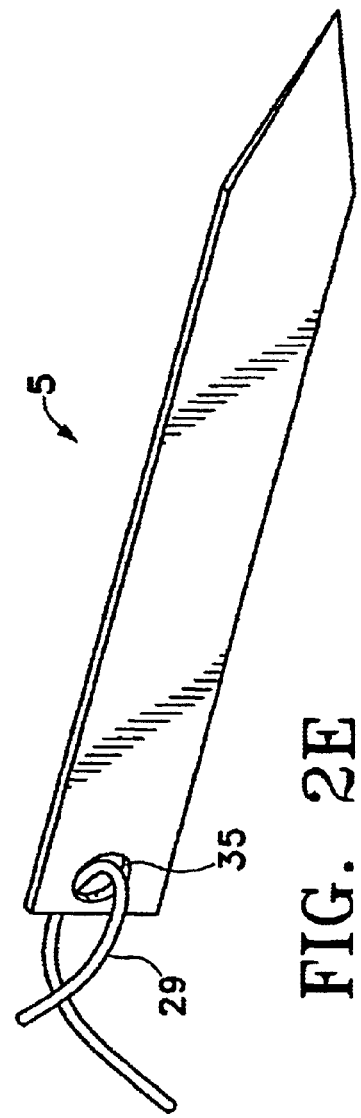
FIG. 2E is yet another embodiment of a locator element according to the present invention connected to a flexible wire or suture.
Figure 2D:
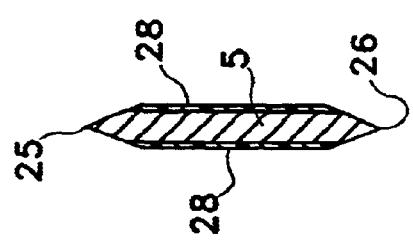
FIG. 2D is a cross-sectional view of the locator element of FIG. 2C.

One particularly useful variation of this configuration is shown the FIG. 2D cross-section of a distal portion 22 of locator element 5 that may be used with RF energy. Here, an insulative coating or layer 28 covers the two opposing surfaces of the locator element 22 adjacent leading edge 25 and trailing edge 26. Such insulation 28 serves to electrically isolate the surfaces covered by the insulation and further focuses the RF energy on the leading and trailing edges. Insulation 28 may comprise a biocompatible polymer or any other suitable biocompatible electrically insulating material. Insulation 28 may be in the form of a coating that may be applied by well known deposition methods such as physical vapor deposition (including sputtering, evaporation, ion plating, ion beam-assisted deposition, ion implantation, etc.), diffusion (e.g., cementation), electrophoresis, anodizing, plating, chemical vapor deposition, pulsed laser deposition, painting, dipping, electroplating, laser surface processing, thermal spraying, etc. Insulation 28 may also be formed in situ via surface oxidation, etc. Insulation 28 may completely cover the opposing surfaces of distal portion 22 as shown in FIG. 2D; alternatively, insulation 28 may cover only portions of these surfaces or additionally cover portions of leading edge 25 and trailing edge 26. The amount of surface area covered by insulation 28, as well as the insulation thickness, compositional profile, density, and other properties may be tailored for the particular tissue and application in which the locator element 5 is designed to operate.

We prefer that insulative coating 28 has a low coefficient of friction to ease the movement of locator element through tissue and within the delivery cannula or sleeve. It is even contemplated that the locator element be coated with a noninsulative but low-friction coating, whether the device is used with RF or other energy or not, simply to achieve this goal.

In application where local tissue damage, either through ablation or local tissue heating due to ablation, is of concern, it may be preferable to insulate all the surface of the locator element 5 that comes into contact with tissue except the distal end of the locator element. This allows the ablation energy to be focused at the distal end of the locator element, allowing for cutting current to focus at the tip. This configuration also has the benefit of achieving a high level of ablation current at the distal end minimal power output, and thus minimizing heating of surrounding tissue since the ablation surface is minimized.

FIG. 2E shows another variation of locating element 5 in which a flexible wire, cable, suture or the like 29 is attached to locator element via eyelet 35. As may be seen, the overall length of locator element 200 may be considerably shorter than other variations, as the cable 29 may be viewed as taking the place of locator element proximal section 21. A suture 29 is even more suitable than the proximal portion shown in FIG. 2A for presenting a flexible, safe, and effective "lead" that may extend out through the breast surface after the locator element has been placed in the tissue. Although not shown, the ends of the wire 29 may be twisted together so that they exit the body as a unit rather than as two separate wires. Additionally, wire 29 may be intentionally kinked in the region of eyelet 35 to help keep it in place.

We find it useful to incorporate an anchoring feature to the locator element 5 to provide enhanced traction when the element is deployed in tissue. The simple shoulder feature described above works well to accomplish this goal.

Although a ribbon shaped locator element is preferred in many applications, a locator element with an oval shaped cross section or circular shaped cross section with an elongated wire like body may be preferable in some applications. In situation where the locator element is used to deliver electromagnetic wave, an antenna shaped locator element may be particular useful.

Figure 3:
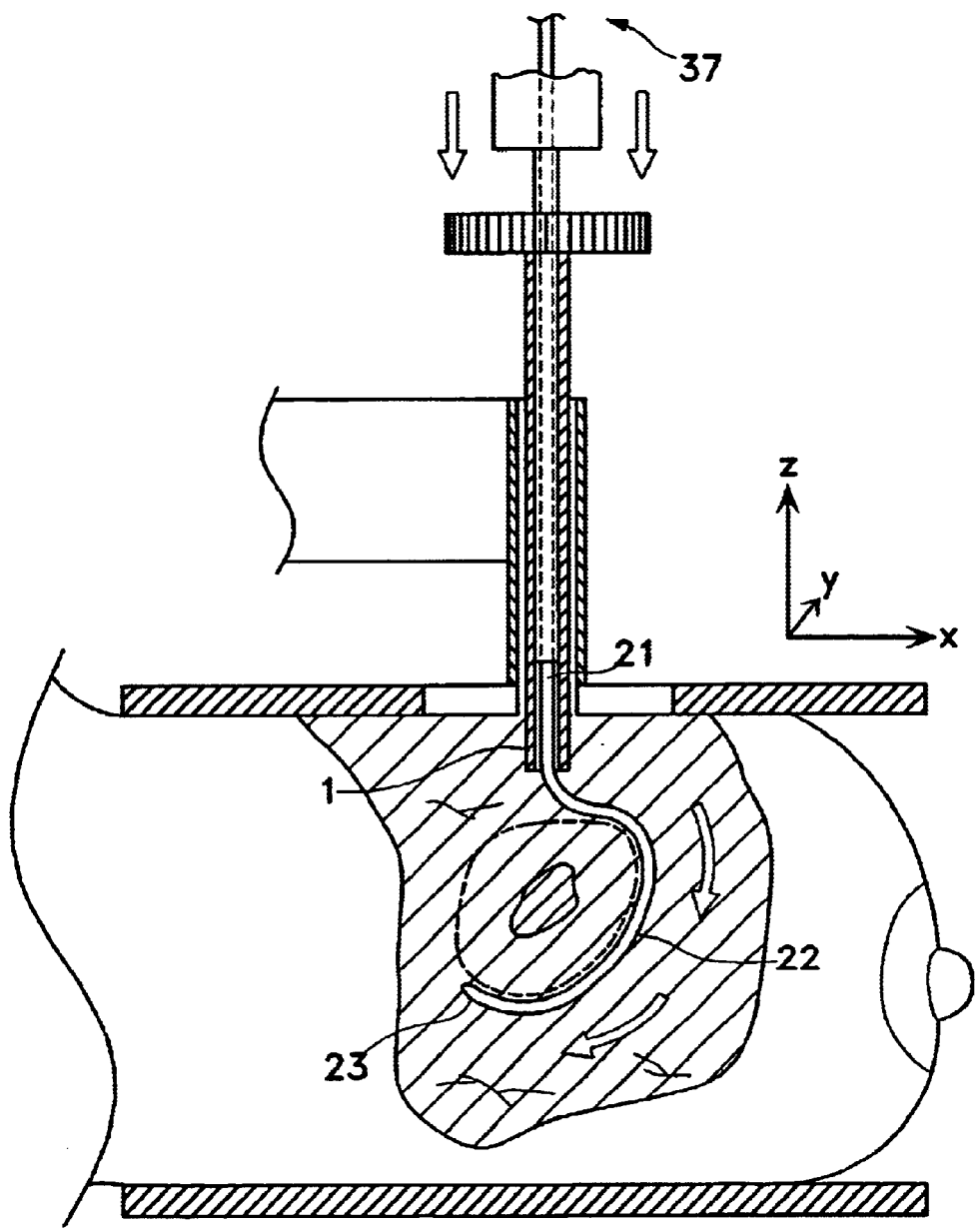
FIG. 3 illustrates one variation of a tissue-localizing device with its locator element deployed in the breast tissue.
Figure 4:
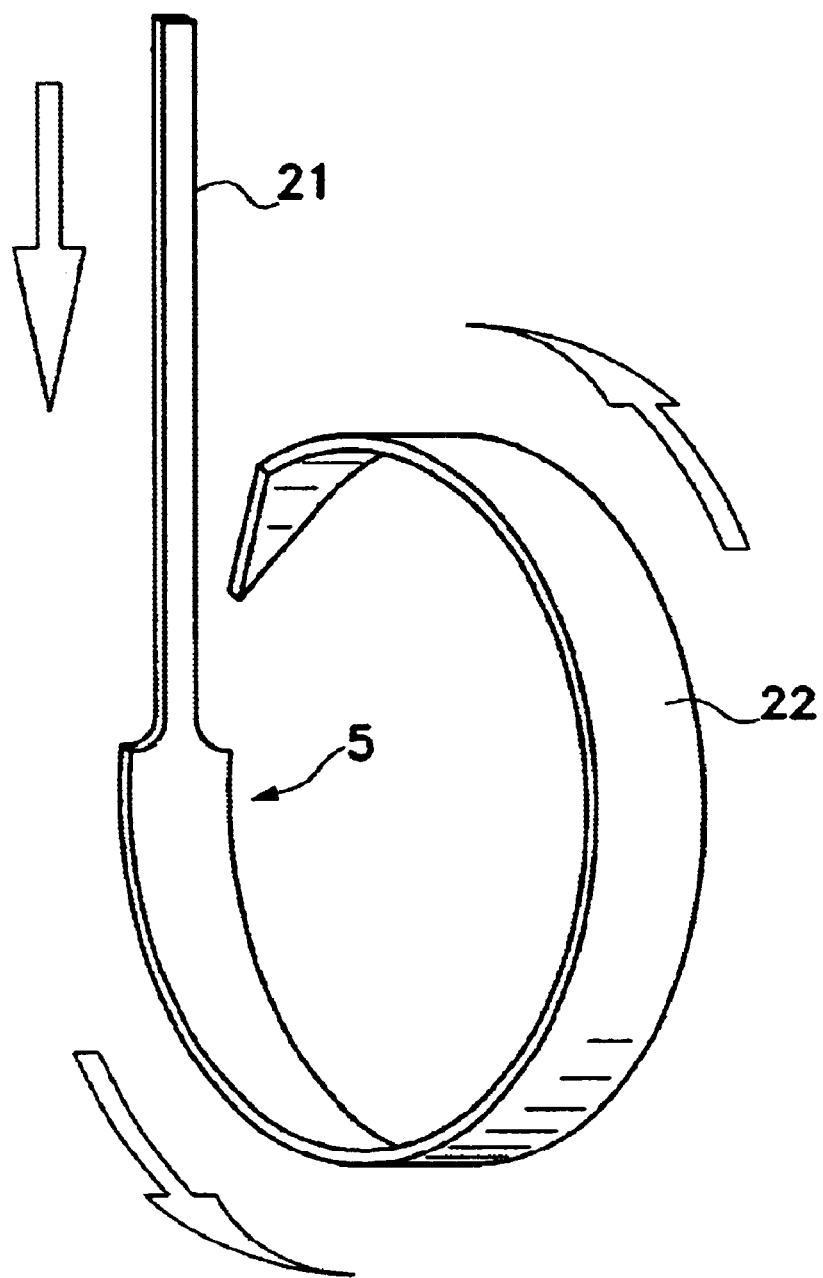
FIG. 4 illustrates a variation of a tissue locator element according to the present in its deployed position.

As described above, the locator element generally has a distal end 23, a proximal end 37, a distal portion 22 and a proximal portion 21, as seen in FIG. 3. The distal portion generally includes the part of the locator element that is inserted in the tissue and forms a loop or a partial loop inside the tissue. The proximal portion is generally the part of the locator element that stays inside the sleeve and does not come into contact with the tissue. FIG. 4 illustrates an alternative variation of a deployed locator element with the distal portion 22 forming a loop that is different form FIG. 3.

In application where a RF current is to be delivered to the tissue, it is preferable that the locator element 5 has a conductive surface that may come in contact with the tissue when it is deployed in the subject's body. The conductive surface may be achieved through coating the body of a locator element with conductive material such as gold, silver, copper, or chrome. Conductive polymer may also be used as coating to achieve surface conduction. Other materials well know to one skilled in the art may also be used to coat the locator element.

Figure 5:
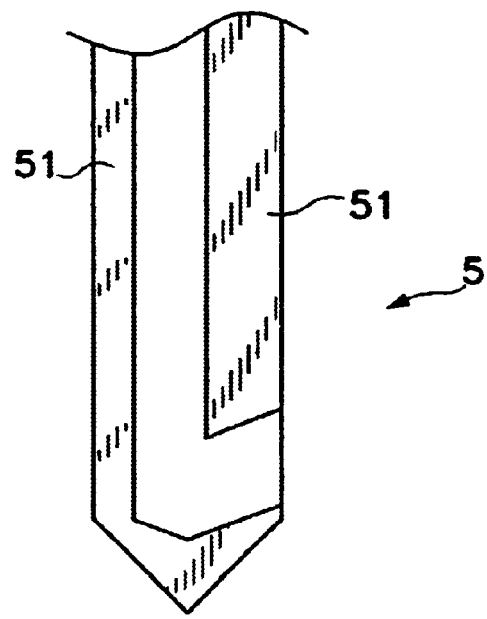
FIG. 5 is a view of a variation of a locator element according to the present invention with two conductive regions.
Figure 6:
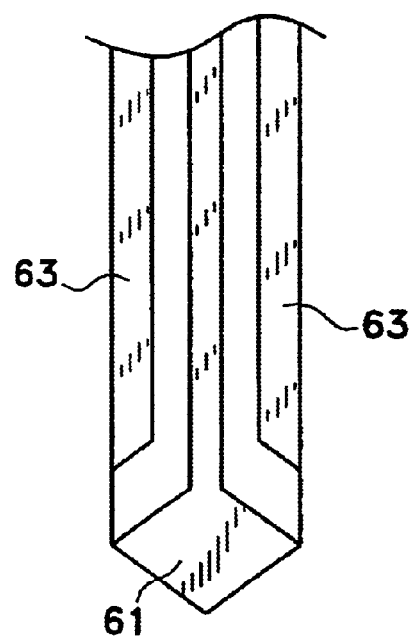
FIG. 6 is a view of another variation of a locator element according to the present invention with three conductive regions.

In some applications, it may be preferable to have a locator element 5 with multiple conductive regions that are electrically isolated from each other. For example, a locator element with two conductive regions 51, such as one shown in FIG. 5, may be desirable in a bipolar application. Locator element 5 with three or more conductive region 51 may also be made through methods well know to one skill in the art. For example, FIG. 6 illustrates an example of a locator element with three conductive regions. The tip region 61 and the two side regions 63 may be energized simultaneously or separately. In a monoplar application, the tip region 61 may be charged for insertion of the locator element, and the side regions 63 are charged when the locator element is rotated to localize the volume of targeted tissue. In a bipolar application, the tip region may serve as one electrode and the two side regions may serve as the second electrode.

Alternatively, the two sides of the locator element may have separate conductive regions. For example, FIG. 7A illustrates one side of the locator element with a conductive surface, and FIG. 7B shows a separate conducting surface located on the opposite side of the locator element shown in FIG. 7A.

FIG. 8 illustrates an example of a locator element with a plurality of conductive regions 51. The various regions may be charged simultaneously or one after another. A controller with a time multiplexer may be used to charge the conductive region in a parallel or sequential pattern as desired by the designer of the device. The specific charging pattern may be selected to enhance efficient penetration or cutting with the locator element and to minimize damage to the surrounding tissue.

Various methods well know to one skilled in the art may be applied to manufacture the conducting surface on the locator element. For example, physical vapor deposition (including sputtering, evaporation, ion plating, ion beam-assisted deposition, ion implantation, etc.), diffusion (e.g., cementation), electrophoresis, anodizing, plating, chemical vapor deposition, pulsed laser deposition, painting, dipping, electroplating, laser surface processing, thermal spraying, are some of the common techniques that may be applied to generate conductive surface on the locator element.

The conducting surface may have a particular pattern or distribution for focusing or dispersing the electric energy. For example, the locator element may have a conductive surface on only one side of the locator element (e.g. the inner circumferential surface when the locator is deployed) to facilitate the localization of RF energy within the volume defined by the deployed locator element.

Figure 9:
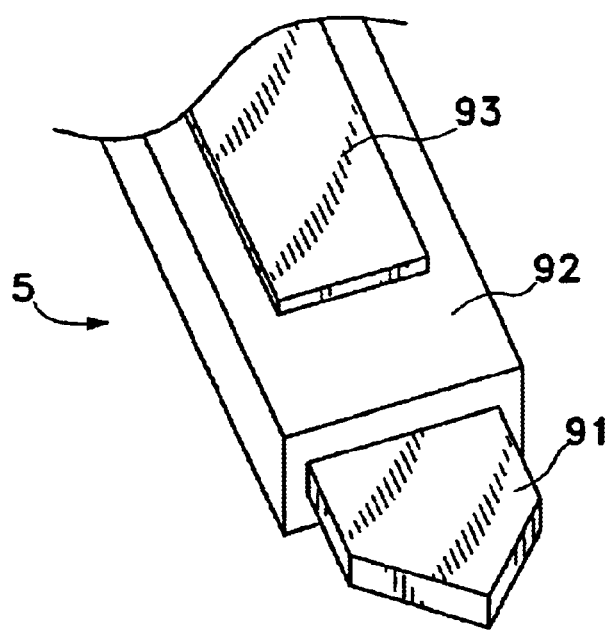
FIG. 9 shows yet another variation of a locator element according to the present invention with two conductive electrodes separate by an insulating layer.

The electric conductive locator element may also be fabricated through layering of conductive material on the locator body. For example, as illustrated in FIG. 9, locator element body 91 constructed of highly conductive metal alloy, may have an insolating layer 92 deposit over its surface, a thin film of metal 93 may then be deposited on top of the insulating layer to create the second electrode. Additional insulating layer may be deposited on top of the second layer to limit the exposed conductive surface as needed.

Figure 10:
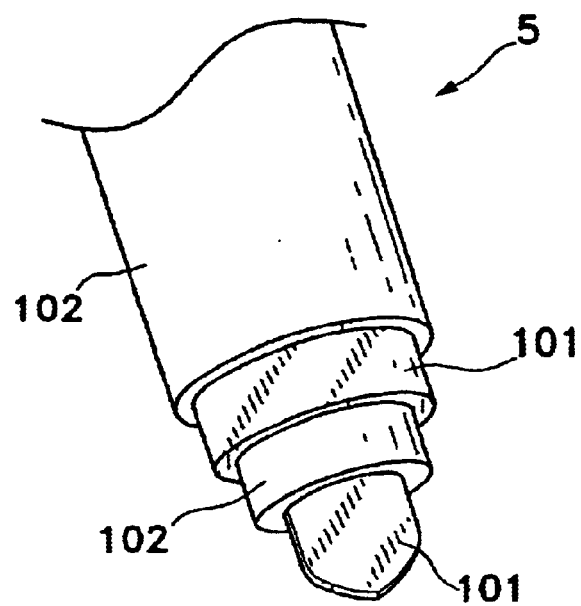
FIG. 10 show a further variation of a locator element according to the present invention with multiple conductive regions comprised of a plurality of coaxial layers.

Coaxial layering of conductive 101 and nonconductive 102 material may also be used to fabricate the locator element 5. An example of a coaxially layered conductive locator element is shown in FIG. 10. The coaxial conductive locator element may have a circular or oval cross-section or it may noncircular such as the example given in FIG. 10.

Figure 11:
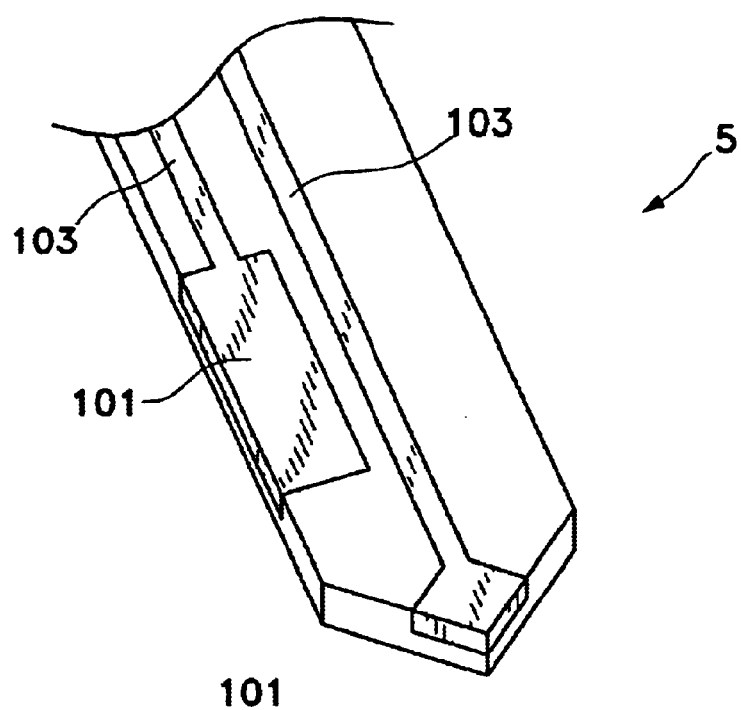
FIG. 11 illustrates yet another variation of a conductive locator element according to the present invention having embedded conductive members.

The locator element 5 may also be constructed by embedding conductive materials 101 on a locator element body. If the locator element body is semiconductive or conductive, the conductive material may be insulated for the body of the locator element when it is integrated with the body. For example, the body of the locator element may be constructed of a non-conductive super-elastic polymer body with two electric conductive wiring 103 embedded in it, as seen in FIG. 11. Two conductive plates are connected to the wiring and disposed at the distal end of the locator element to serve as the energizing surface. Additional two conductive plates are located at the proximal end of the locator element and connected to the wiring to serve as contact points for connection to the power supply.

An insulating layer may be deposited through various methods well know to one skilled in the art. For example, a polymer layer may be directly deposited on the locator element as an electric insulating layer. Heat shrink tubing may also be used to provide the insulating layer on the locator element.

Figure 12:
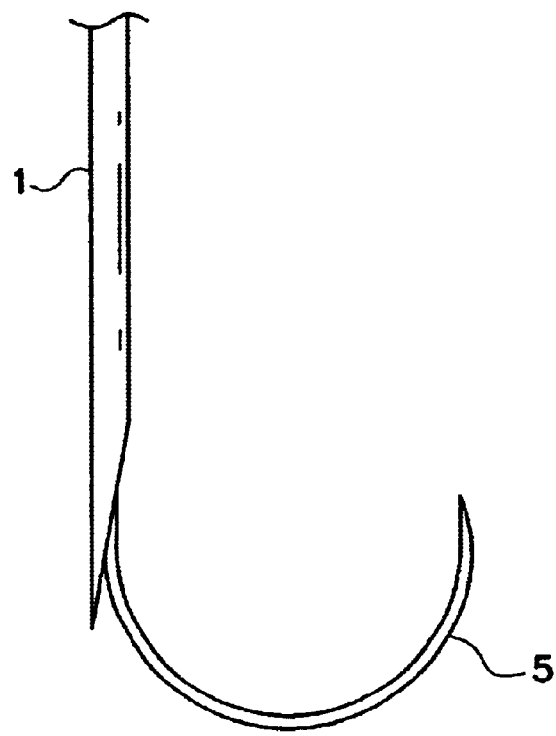
FIG. 12 is a view of a partially deployed locator element extending from the sleeve of the tissue-localizing device of FIG. 1.

Sleeve 1 has a distal end, a proximal end, an inner surface, an outer surface, and allows a locator element to be slidably located within its lumen, as shown in FIG. 12. In one variation, the sleeve is an electrically conductive cannula. Alternatively, the conductive surface may be placed or deposited on the sleeve through methods well known to one skill in the art. For example, methods such as electroplating, electrodeposition and plasma deposition may be used to create the conductive region on the surface of the cannula. Conductive members, such as metal wiring or electrode may also be integrated with the sleeve to provide the conductive region on the surface of the sleeve.

When the sleeve is comprised of a conductive material, it is preferable that an insulating liner is placed in the inner surface of the sleeve. The insulating liner may be comprised of a non-conductive polymer and/or other material with low conductivity that are well known to one of skill in the art and which are suitable for such purpose. Biocompatible plastics such as polyethylene, polypropylene, polyvinylchloride (PVC), ethylvinylacetate (EVA), polyethyleneterephthalate (PET), polytetrafluoroethylene, polyurethanes, polycarbonates, polyamide (such as the Nylons), silicone elastomers, and their mixtures and block or random copolymers may be applied on the inner surface of the sleeve as an insulating layer and/or as a protective coating between the the locator element and the sleeve.

It may be desirable to monitor the temperature of locator element 5 and/or the tissue surrounding the location where the locator element is deployed. Such data may be obtained through placement of a temperature sensor on the locator element 5 or the sleeve 1 of the tissue-localizing device. The temperature sensor may be a semiconductor-based sensor, a thermister, a thermal couple or other temperature sensor that would be considered as suitable by one skilled in the art. An independent temperature monitor may be connected to the temperature sensor. Alternatively, a power supply with an integrated temperature monitoring circuit, such as one described in U.S. Pat. No. 5,954,719, which is incorporated by reference herein, may be used to modulate RF power output supplied to the locator element. Other physiological signals, e.g. EKG, may also be monitored by other medical instrumentation well known to one skilled in the art and such data applied to control the RF energy delivered to the locator element. Alternatively, the temperature sensor may be adapted to monitor the temperature of the locator element.

Figure 13:
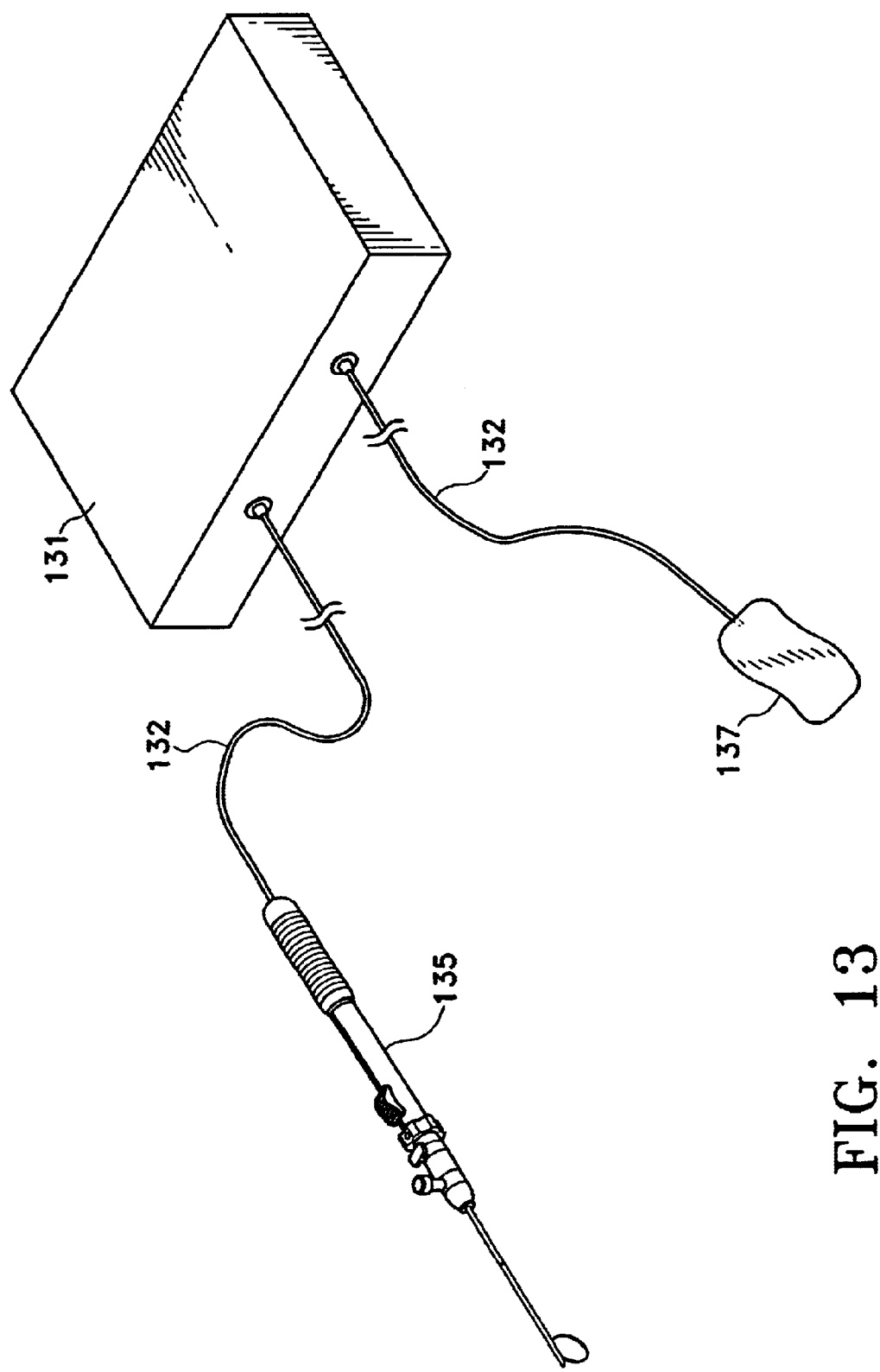
FIG. 13 illustrates a system configuration implementing a monopolar tissue-localizing device according to the present invention including a conductive pad for connection to the subject's body.

The energized tissue-localizing device may be implemented with a bipolar or a monopolar configuration. In a mopolar configuration, it may be preferable to establish a separate electric connection from the body of the subject to the power supply. FIG. 13 illustrates one such monpolar configuration. The RF ablation generator 131 has two separate electric conduction paths 132. One is connected to the tissue-localizing device 135 and a second connection is connected to a conductive pad 137. The conductive pad 137 is to be placed on a body surface of the subject to provide the ground, or negative electric connection so the ablation current has a return path to the power supply. Other conductive material or electrode may also be used to provide the connection to the body of the subject.

In a bipolar configuration, it is preferable that the sleeve 1 of the tissue-localizing device serves as the second electrode. Alternatively, as described earlier, both electrodes for the bipolar configuration may be located on the locator element if the locator element has more than one conductive region. FIG. 14 shows an example of a bipolar device where a separate electric plug 141 is provided for the connection to the power supply. Plug #1 141 is connected to the locator element and plug #2 142 is connected to the sleeve. In this configuration, the sleeve is preferably a conductive needle cannula.

In another variation, a light-transferring medium, such as an optical fiber, is provided on the locator element enabling delivery of light to the localized tissue. photodynamic therapy (PDT) has been shown to be a very effective method for treating tumors. PDT has also been proposed for treatment of cardiovascular disease, particularly atherosclerosis. PDT employs photosensitive target-selective molecules, which are injected into the blood and selectively concentrated at a particular treatment sight where they may be photoactivated to initiate target cell destruction. Alternatively the light transferring system may also be used for hypothermia therapy. Conduction of light from a source, such as a laser, to the treatment site may be accomplished through the use of a single or multiple fiber optic delivery system with special diffuser treatment tips. Balloon catheters, such as one described in U.S. Pat. No. 5,700,243 to Narciso, Jr. which is incorporated herein by reference, had been adapted to direct photons for PDT. However an efficient means to deliver PDT to tissues located away from the major vessels is still need. The locator element with an integrated light transfer medium provides an excellent solution through a minimally invasive procedure that overcomes difficulties in reaching tissues outside of the vessels.

Photon transferring medium, such as optical fibers may be integrated with the locator element. Light diffuser element may be adapted to the distal portion of the locator element when light diffusion is desired. Some examples of a light diffuser include a single fiber cylindrical diffuser, a spherical diffuser, a microlensing system, an over-the-wire cylindrical diffusing multi-fiber optic catheter, etc. U.S. Pat. No. 6,027,524 to Petit, also disclosed a fiber-optic light transfer system with a diffuser tip, which is incorporated herein by reference. Alternatively, the locator element may be constructed of a light transferring medium. In one variation of a locator element adapted for PDT, one or more optical fibers are annealed to the inner surface of the locator element. Light diffusing elements are adapted to the distal end of the optical fibers. The locator element may be deployed around the tissue of interest, and a photon source, e.g. laser, UV, etc., may be employed at the proximal end of the optical fibers to supply the excitation light to the targeted tissue. A special adapter may be integrated into the pusher assembly for connecting the optical fibers to the photon source.

A monopolar tissue-localizing device according to the invention can be used to localize tissue in the following manner. An electric conductive pad and a tissue-localizing device with an energizable locator element are connected to a RF ablation generator. With x-ray imaging, the user locates the region of interest within a subject's body. Other imaging devices, such as an ultrasound imager or MRI may also be used for the purpose of locating the tissue of interest and assisting in the deployment of the locator. The electric conductive pad is then secured to the body of the subject. After application of local anesthesia, the user then inserts the sleeve of the tissue-localizing device into the tissue, placing the distal end of the locator element adjacent to the region of interest. The locator element is then slowly deployed from the sleeve. As the locator element is advanced forward, the tip of the locator element is energized intermittently or continuously to facilitate the penetration of the locator element into the tissue and to induce coagulation of the damaged vessels. When the locator element is completely deployed, it forms a partial loop around the region of interest. The locator element is then detached from the tissue-localizing device. The tissue-localizing device, along with its sleeve is removed from the subject's body leaving the locator element in the tissue marking the region of interest.

A bipolar device according to the present invention can likewise be used in a similar manner. The user locates the tissue of interest as described above. Since the bipolar device has both conducting paths located on the tissue-localizing device itself, a separate conductive pad is not necessary. As described above, the user then inserts the sleeve of the locator element into the tissue. In some applications where the tissue is particularly dense, it may be necessary to energize the sleeve of the tissue-localizing device to facilitate the insertion of the sleeve into the tissue. After the sleeve is in place, the locator element is deployed into the tissue to surround the region of interest. As the user experiences resistance in advancing the locator element, RF energy may be delivered to the locator element to facilitate the insertion of the locator element. Once the locator element is deployed, it is disconnected from the tissue-localizing device and the sleeve of the tissue-localizing device is then withdrawn form the subject body.

As described, a tissue-localizing device according to the present invention can be provided with an integrated temperature sensor. In use, the tissue-localizing device is inserted into the tissue and the locator element is deployed as previously described. However, in such methods, for example, a RF ablation generator with a built-in close-loop temperature control mechanism can be used to modulate the RF current delivered to the locator element. A thermocouple integrated with the sleeve of the tissue-localizing device can provide the temperature measurement to the close-loop controller. The RF energy output is modulated depending on the temperature information provided by the thermal couple. As the user advances the locator element into the tissue, the RF generator provides pulses of RF energy to cut through the tissue, the RF energy pulse is modulated so as not to over heat the surrounding tissue.

It is well known that ultrasound and other RF energy directed at a tissue may facilitate the absorption of chemicals or medication. In this example, ultrasound is directed at a volume of tissue to facilitate the absorption of the drug in the tissue and also to activate the drug within this tissue. It is contemplated that the tissue-localizing device or the electric conductive locator element of the present invention may be used to direct RF energy locally for the sole purpose of drug activation, or to facilitate absorption only. Furthermore, the tissue-localizing device may be used to direct RF energy to heat a designated volume of tissue. It is well known in the scientific community that heating of certain malignant tissue could have significant therapeutic effect.

Encapsulated gas microbubbles are well known in the scientific community as vehicle for transporting drug or chemical in the blood. Such bubbles, with an average size less than that of a red blood cell, are capable to penetrate even into the smallest capillaries and release drugs and genes, incorporated either inside them or on their surfaces. Moreover, the microbubbles may be used to transport a specific drug to a specific site within the body (for instance, an anticancer drug to a specific tumor) if their surface contains ligands. The ligands (e.g. biotin or antibody) will bind to the receptors (e.g. avidin or antigen) situated at the blood vessel walls of the target site and force the microbubble to attach to the walls. Methods for preparing such microbubbles have already been described in U.S. Pat. No. 6,146,657 to Unger. U.S. Pat. No. 6,245,318 B1 further describe the uses of microbubbles for diagnostic and therapeutic applications. Method of using microbubbles to enhance the bioavailibility of bioactive agents in vivo is described in detail in U.S. Patent Application Pub. No. US 2001/0051131 A1 to Unger. The above cited patents and patent application are hereby incorporated by reference in their entirety.

The microbubbles may serve as vehicles for carrying drug or gene in the blood stream. The microbubbles may remain stable long enough to circulate and accumulate at the binding site. They are able to reach the target tissue and diffuse into the target tissue. Ultrasound energy may then be applied to rupture the microbbubles in the target tissue and forcing the release of the drug or gene carried by the microbbubles.

As an example, a tissue-localizing device with a conducting locator element, which is adapted to serve as an antenna to deliver ultrasound energy can be deployed around a target tissue site containing a malignancy. Microbbubles carrying small molecule chemotherapy agents can be injected into the subject and the microbubbles allowed to diffuse. The locator element can then be energized to create a localized ultrasound energy field to rupture the microbubble carriers that have diffused into the localized energy field releasing the chemotherapeutic agents at the malignancy site.

It is understood that the above example only suggests one of many possibility of utilizing the energizable tissue-localizing device for local drug activation. Other RF electromagnetic waves may also be implemented on tissue-localizing devices to facilitate chemical absorption and/or activate chemical activities within a localized tissue. Other carriers or chemical compositions that may be activated by RF energy may also be suitable in local drug activation applications.

Alternatively, a RF antenna or electrode may also be deployed around a vessel to activate a drug that flows through that particular vessel. For example, the locator element may be deployed around, say, the right femoral artery in the leg. Inactivated drugs are then injected into a vein in the forearm of the patient. The RF energy is then delivered to the locator element to activate drugs that flow down the right femoral artery.

This invention has been described and specific examples of the invention have been portrayed. The use of those specifics is not intended to limit the invention in anyway. Additionally, to the extent there are variations of the invention, which are within the spirit of the disclosure or equivalent to the inventions found in the claims, it is our intent that this patent will cover those variations as well.

We claim the following:

1. A tissue-localizing device comprising:

a sleeve having a lumen;

a locator element at least partially disposed in the lumen of said sleeve in a slidable manner, said locator element having a distal portion and a distal end, the distal portion having a discrete electric conductive surface region at or near said distal end, the locator element further being adapted to penetrate tissue so that the distal portion of the locator element forms at least a partial loop that defines a volume of tissue when said locator element is deployed in tissue; and an insulating layer at least partially covering an inner surface of said sleeve.

2. A tissue-localizing device comprising:

a sleeve having a lumen and an insulating liner covering the inner surface of said sleeve;

an electric conductive locator element at least partially disposed in the lumen of said sleeve in a slidable manner, said locator element having a distal portion, the locator element further being adapted to penetrate tissue so that the distal portion of the locator element forms at least a partial loop that defines a volume of the tissue when said locator element is deployed in the tissue;

wherein said sleeve is electric conductive; and an insulating layer covering an outer surface of said sleeve with a distal end of said sleeve exposed.

* * * * *